US00PP08804P

United States Patent [19]

VandenBerg

[11] Patent Number: Plant 8,804

[45] Date of Patent: Jun. 28, 1994

[54] CHRYSANTHEMUM PLANT NAMES YELLOW SARAH

[75] Inventor: Cornelis P. VandenBerg, Salinas, Calif.

[73] Assignee: Yoder Brothers, Inc., Barberton, Ohio

[21] Appl. No.: 982,952

[22] Filed: Nov. 30, 1992

[51] Int. Cl.[5] ..... A01H 5/00

[52] U.S. Cl. ..... Plt./78

[58] Field of Search ..... Plt. 78, 79

[56] References Cited

U.S. PATENT DOCUMENTS 4,616,099 10/1986 Sparkes ..... 47/58

OTHER PUBLICATIONS

Broertjes, et al., 1980, "Amutant of a mutual of a . . . Irradiation of progressiive radiation-induced mutants in a mutation breeding programme with *Chrysanthemum morifolium*", Euphytica 29:526–530.

Gosling et al., "The Chrysanthemum Manual-6th edition", The National Chrysanthemum Society, London, Essex Telegraph Press, Ltd., pp. 329–336.

Broertjes, et al., 1978, "Application of Mutation Breeding Methods in the Improvement of Vegetatively Propagated Crops", Elsevier Sci. Pub. Co., New York, pp. 162–175.

Searle, et al., 1968, "Chrysanthemum the Year Round", Blanford Press, London, pp. 27–29, 320–327.

Chan, 1966, "Chrysanthemum and rose mutations induced by X-rays", Am. Soc. Hort. Sci. Proc., pp. 613–620.

Broertjes, 1966, "Mutation breeding of chrysanthemums", Euphytica, 15:156–162.

Dowrich, et al., 1966, "The induction of mutations in Chrysanthemum using X-and gamma radiation", Euphytica, 15:204–210.

*Primary Examiner*—Howard J. Locker

*Attorney, Agent, or Firm*—Foley & Lardner

[57] ABSTRACT

A Chrysanthemum plant named Yellow Sarah particularly characterized by its flat capitulum form; quilled decorative capitulum type; yellow ray floret color; diameter across face of capitulum of 63 to 75 mm when fully opened; branching pattern is spreading and prolific, with 7 to 10 breaks after pinch when grown outside under natural daylength in fall flowerings, and 5 to 6 breaks after pinch when grown in 10 cm pots for spring flowerings; natural season flower date of August 27 when planting rooted cuttings on June 25 in Salinas, Calif., and October 12 to 14 when planting rooted cuttings June 15 in Hightstown, N.J.; Flowering response of 49 days after rooting in no light/no shade programs in spring in Salinas, Calif.; plant height of 25 to 33 cm when grown in fall under natural daylength with no growth regulators, and 18 to 20 cm when grown in 10 cm pots in spring with no growth regulator applications; and durable, uniform performance.

2 Drawing Sheets

The present invention comprises a new and distinct cultivar of Chrysanthemum, botanically known as *Dendranthema grandiflora*, and referred to by the cultivar name Yellow Sarah.

Yellow Sarah, identified as 8497 (85-070G04), is a product of a mutation induction program. The new cultivar was discovered and selected by Cornelis P. VandenBerg on Nov. 13, 1989, in a controlled environment in Salinas, Calif. as one flowering plant within a flowering block established as rooted cuttings from stock plants which had been exposed as unrooted cuttings to an X-ray source of 1500 rads in Forty Myers, Fla. on Jun. 8, 1989. The irradiated parent cultivar was cultivar identified as Sarah, disclosed in U.S. Plant Pat. No. 7,586. Sarah is described as a spray pot mum and garden mum with a flat capitulum form; a quilled decorative capitulum type; a butterscotch-bronze ray floret color; diameter across face of capitulum of 63 to b 75 mm when fully opened; spreading and prolific branching pattern, with 7 to 10 branches after pinch; average natural season flower date of August 27 to September 4 in Salinas, Calif. and October 3 to 14 in Hightstown, N.J.; photoperiodic flowering response to short days in photoperiodic controlled flowering programs of 49 to 52 days; and durable, uniform performance. The above description of Sarah has a slightly wider range of values than disclosed in U.S. Plant Pat. No. 7,586 for Sarah, based on continued flower trials after the application for Sarah was filed.

The irradiation program resulting in Yellow Sarah had as its primary objective the expansion of color ranges of the parent cultivar Sarah. The irradiation program comprised irradiating cuttings of the parent cultivar at irradiation levels of 1500, 1750 and 2000 rads. A total of 1111 cuttings harvested from a total of 225 irradiated plants were planted on Sep. 11, Sep. 4 and Aug. 21, 1989, respectively. Of these, 18 initial selections were made, which selections were then revegetated and reflowered. Four consecutive flowerings resulted in discarding 15 of the original 18 selections on Aug. 29, 1990. One selection, 8429, was reselected under code number 8497, while the original selection 8429 was discarded. Four selections, including the new reselection, were made PIs (Possible Introductions) after the fourth flowering on Aug. 29, 1990 and trialed for one year, ultimately resulting in discarding three of these four remaining selections and the decision to introduce the one remaining selection as Yellow Sarah.

The first act of asexual reproduction of Yellow Sarah was accomplished when vegetative cuttings were taken from the reselection on November 1990 in a controlled environment in Salinas, Calif., by technicians working under supervision of Cornelis P. VandenBerg.

Horticultural examination of controlled flowerings of successive plantings has shown that the unique combination of characteristics as herein disclosed for Yellow Sarah are firmly fixed and are retained through successive generations of asexual reproduction.

Yellow Sarah has not been observed under all possible environmental conditions. The phenotype may vary significiantly with variations in environment such as temperature, light intensity and daylength, without, however, any variance in genotype.

The following observations, measurements and comparisons describe plants grown in controlled open areas in Salinas, Calif., and in Hightstown, N.J. Rooted cuttings were established in soil and maintained outdoors under the natural temperatures and daylength prevailing during June through October. Spring flowerings were conducted in Salinas, Calif. under greenhouse conditions which approximate those generally used in commercial practice for small pot spring garden mum production.

The following traits have been repeatedly observed and are determined to be basic characteristics of Yellow Sarah, which, in combination, distinguish this chrysanthemum as a new and distinct cultivar:

1. Flat capitulum form.
2. Quilled decorative capitulum type.
3. Yellow ray floret color.
4. Diameter across face of capitulum of 63 to 75 mm when fully opened.
5. Branching pattern is spreading and prolific, with 7 to 10 breaks after pinch when grown outside under natural daylength in fall flowerings, and 5 to 6 breaks after pinch when grown in 10 cm pots for spring flowerings.
6. Natural season flower date of August 27 when planting rooted cuttings on June 25 in Salinas, Calif., and October 12 to 14 when planting rooted cuttings June 15 in Hightstown, N.J.
7. Flowering response of 49 days after rooting in no light/no shade programs in spring.
8. Plant height of 25 to 33 cm when grown in fall under natural daylength with no growth regulators, and 18 to 20 cm when grown in 10 cm pots in spring with no growth regulator applications.
9. Durable, uniform performance.

In the accompanying photographic drawings the photo on sheet 1 is a color photograph of Yellow Sarah grown as a pinched garden mum under natural season outside conditions in Salinas, Calif., with the colors being as nearly true as possible with illustrations of this type.

The photo on sheet 2 comprises a color photograph taken in a spring flowering program in Salinas, Calif., comparing Yellow Sarah (on left) to Sarah (on right). The siginficant differences in ray floret colors between the new cultivar and its parent will be readily apparent.

Of the commercial cultivars known to the inventor, the most similar in comparison to Yellow Sarah is the parent cultivar Sarah. All traits of Yellow Sarah are similar to those of Sarah, except for the ray floret color. When grown under conditions other than high light and high temperature, the ray floret color of Yellow Sarah is yellow, while the ray floret color of Sarah is butterscotch-bronze. During high light and high temperatures in summer, Yellow Sarah substantially maintains its bright yellow color whereas the ray florets of Sarah fade from butterscotch-bronze (inside surface of tubes is 22A, with outside surface of tubes being closest to 20B) to almost yellow.

In the following description color references are made to The Royal Horticultural Society Colour Chart. The color values were determined on plant material grown as a pinched garden mum grown under natural season outside conditions in Salinas, Calif. on Sep. 2, 1992.

Classification:

*Botanical.*—*Dendranthema grandiflora* cv Yellow Sarah.

*Commercial.*—Flat quilled decorative spray pot mum and garden mum.

INFLORESCENCE

A. Capitulum:

*Form.*—Flat.

*Type.*—Quilled decorative.

*Diameter across face.*—63 to 75 mm when fully opened.

B. Corolla of ray florets:

*Color (general tonality from a distance of three meters).*—Yellow.

*Color (upper surface).*—Center ray florets closest to 13B. Outer ray florets maturing to b 12B to 13C. Under low temperature conditions immature buds and underside of outer ray florets exhibit a slight bronzing.

*Color (under surface).*—12B to 13C.

*Shape.*—Tubular, straight.

C. Corolla of disc florets:

*Color (mature).*—14A to 14B.

*Color (immature).*—Closest to 14B, slightly tinged with 144C.

D. Reproductive organs:

*Androecium.*—Present on disc florets only; scant pollen.

*Gynoecium.*—Present on both ray and disc florets.

PLANT

A. General appearance:

*Height.*—25 to 33 cm when grown in fall under natural daylength with no growth regulators, and 18 to 20 cm when grown in 10 cm pots in spring with no growth regulator applications.

*Branching pattern.*—Spreading and prolific, with 7 to 10 breaks after pinch when grown outside under natural daylength in fall flowerings, and 5 to 6 breaks after pinch when grown in 10 cm pots for spring flowerings.

B. Foliage:

*Color (upper surface).*—147A.

*Color (under surface).*—147B.

*Shape.*—See photograph.

I claim:

1. A new and distinct Chrysanthemum plant named Yellow Sarah, as described and illustrated.

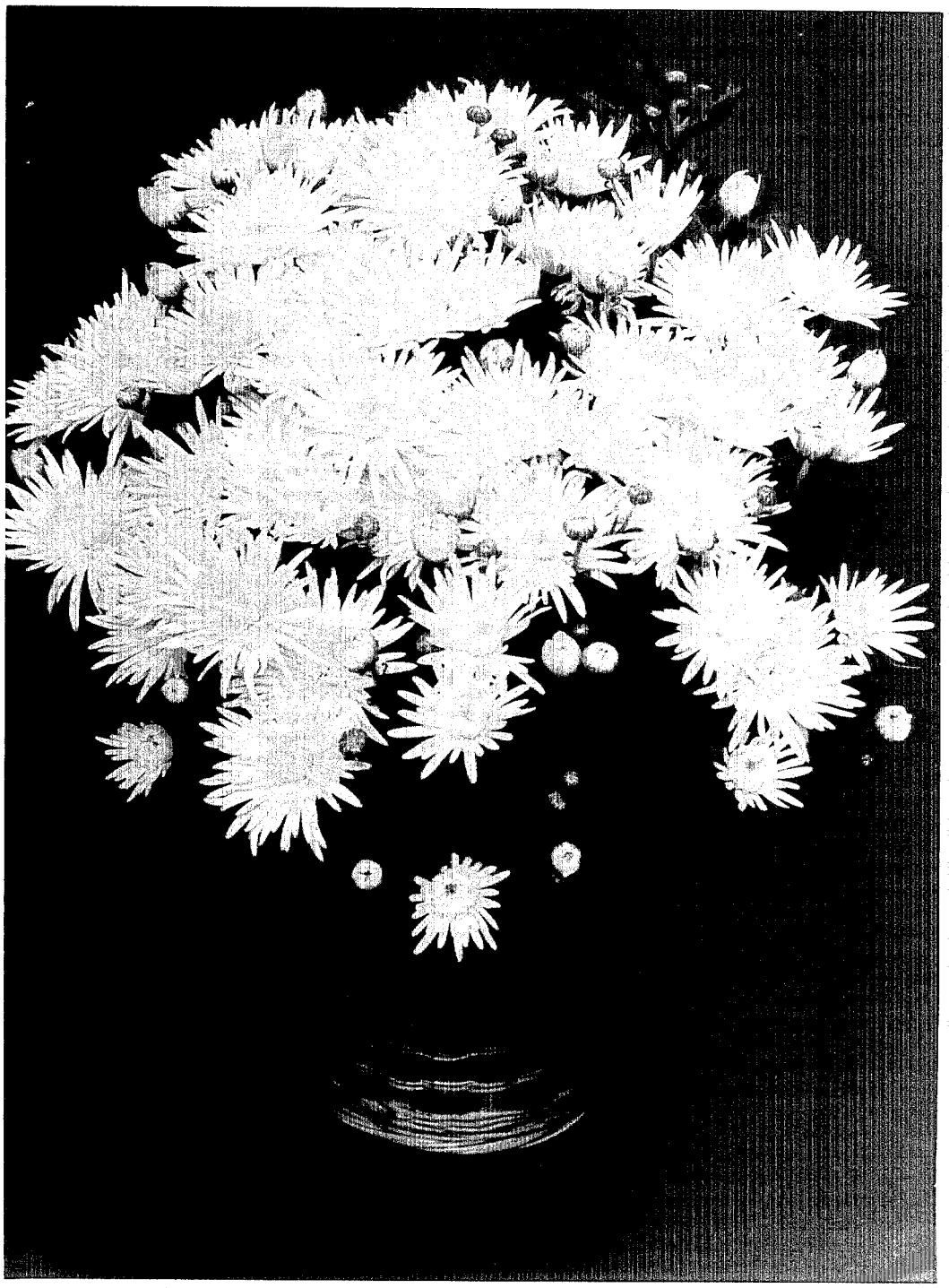

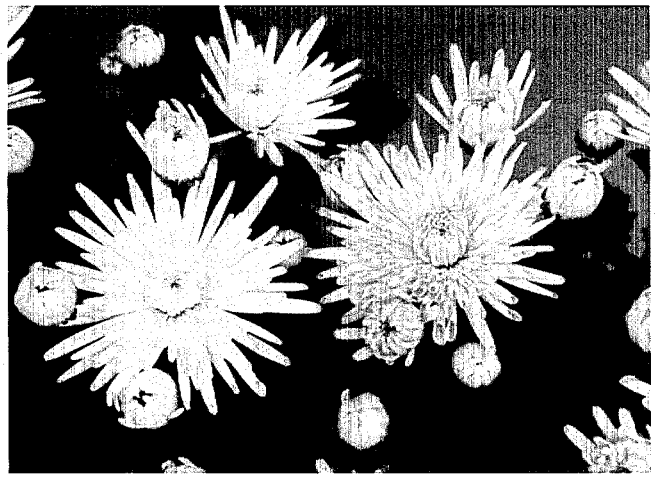

* * * * *